(12) United States Patent
Song et al.

(10) Patent No.: US 11,957,613 B2
(45) Date of Patent: Apr. 16, 2024

(54) WATER AND GAS DUAL-PURPOSE ELECTRIC ERECTION AID

(71) Applicant: SHANGHAI REALOV ELECTRONIC TECHNOLOGY CO., LTD., Shanghai (CN)

(72) Inventors: Xin Song, Shanghai (CN); Dacheng Yang, Shanghai (CN)

(73) Assignee: SHANGHAI REALOV ELECTRONIC TECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 17/440,201

(22) PCT Filed: Aug. 25, 2021

(86) PCT No.: PCT/CN2021/114449
§ 371 (c)(1),
(2) Date: Sep. 17, 2021

(87) PCT Pub. No.: WO2022/127176
PCT Pub. Date: Jun. 23, 2022

(65) Prior Publication Data
US 2022/0401249 A1 Dec. 22, 2022

(30) Foreign Application Priority Data
Dec. 18, 2020 (CN) .......................... 202011507535.X (51) Int. Cl.
*A61F 5/41* (2006.01)
(52) U.S. Cl.
CPC .......... *A61F 5/41* (2013.01); *A61F 2005/412* (2013.01)

(58) Field of Classification Search
CPC ............................. A61F 5/41; A61F 2005/412
See application file for complete search history.

(56) References Cited

U.S. PATENT DOCUMENTS

| | | | | |
|---|---|---|---|---|
| 5,421,808 A * | 6/1995 | Osbon | ..................... | A61H 9/005 600/38 |
| 5,462,514 A * | 10/1995 | Harris | ....................... | A61F 5/41 600/38 |
| 6,183,414 B1 * | 2/2001 | Wysor | .................... | G01N 21/49 600/38 |
| 2006/0089572 A1 * | 4/2006 | Byon | ........................ | A61F 5/41 601/9 |
| 2017/0224522 A1 * | 8/2017 | Irias | ..................... | A61H 9/0057 |
| 2019/0133809 A1 * | 5/2019 | Jochum | ..................... | A61F 5/41 |

* cited by examiner

*Primary Examiner* — Samuel G Gilbert
(74) *Attorney, Agent, or Firm* — Zhu Lehnhoff LLP (57) ABSTRACT

A water and gas dual-purpose electric erection aid includes a vacuum barrel and a device bin, which has a seal cover that covers one end of the vacuum barrel and a pump valve pipeline mechanism arranged in the seal cover and used for vacuumizing the vacuum barrel; the device bin is installed with a button control assembly via a support frame; the seal cover is provided with an open groove exposing a button part of the button control assembly and the open groove is tightly attached to the button control assembly; the pump valve pipeline mechanism is communicated with two connection ports formed at the top of the vacuum barrel and a vent cover fixedly arranged on the seal cover through a connecting pipe. The erection aid can be used both in air and underwater. It has good adjuvant treatment and improvement effects on men suffering from sexual dysfunction.

3 Claims, 6 Drawing Sheets

WATER AND GAS DUAL-PURPOSE ELECTRIC ERECTION AID

TECHNICAL FIELD

The invention belongs to the technical field of erection aid device, and particularly relates to a water and gas dual-purpose electric erection aid.

BACKGROUND ART

If a man has a weak sexual function and cannot erect or be erectile but not rigid, it not only seriously affects harmony and happiness of family life, but also affects learning and work, and increases social instability factors. Erectile dysfunction is generally classified into three categories according to etiology: psychological erectile dysfunction, organic erectile dysfunction and mixed erectile dysfunction (with the concurrence of both organic causes and psychological factors).

However, today's medical clinical treatment of male sexual dysfunction, such as hypofunction and low desire, mainly depends on drugs. Most of the drugs in the market are only used to treat the symptoms without solving root causes, and have toxicity. If people rely on the drugs for a long time, it not only cannot treat the diseases, but also damage the body, which is at cross purpose. Therefore, there are some electric erection aids (penis pump) that physically assist erection in the market.

According to the conventional electric erection aid, the existing electric erection aid can only be used in air. One common side effect of the electric erection aid is that the vacuum negative pressure is too large or the air suction is too fast, so that capillary rupture is easily caused, and penis edema is caused. In addition, some users can feel uncomfortable during the vacuumizing. Therefore, targeted improvement is needed.

SUMMARY OF THE INVENTION

The invention is directed to provide a water and gas dual-purpose electric erection aid, which is used for correcting the defect of male dysfunction, beneficial to promoting the harmony of marriage and families, and contributes to social stability.

In order to achieve the above object, the invention provides the following technical solution. A water and gas dual-purpose electric erection aid comprises a vacuum barrel and a device bin arranged at the top of the vacuum barrel, characterized in that the device bin comprises a seal cover which covers one end of the vacuum barrel and a pump valve pipeline mechanism arranged in the seal cover and used for vacuumizing or releasing vacuum of the interior of the vacuum barrel; and the device bin is fixedly installed with a button control assembly via a support frame, the seal cover is provided with an open groove exposing a button part of the button control assembly, and the inner wall of the open groove is tightly attached to the outer wall of the button control assembly;

the pump valve pipeline mechanism is communicated with a connection port formed in the top of the vacuum barrel and a vent cover on the seal cover via a connecting pipe, and the vent cover is clamped in a step groove of the seal cover by an outer seal ring.

Preferably, the connection port is at least provided with more than one.

Preferably, the connection port is at least provided with two.

Preferably, the pump valve pipeline mechanism comprises two negative pressure pumps and one electromagnetic valve, wherein an air inlet of one negative pressure pump is communicated with one connection port at the top of the vacuum barrel, and an air outlet is communicated with one connector of the vent cover by a connecting pipe; and an air outlet of another negative pressure pump is communicated with another connection port by a connecting pipe, an air inlet is communicated with one valve port of the electromagnetic valve through the connecting pipe, and another valve port is communicated with another connector of the vent cover by a connecting pipe.

Preferably, the pump valve pipeline mechanism comprises one negative pressure pump and two two-position three-way valves, wherein one connection port is connected with one valve port of one of the two-position three-way valves by a connecting pipe, and the other two valve ports are respectively communicated with the vent cover and the air inlet of the negative pressure pump by the connecting pipe; and the air outlet of the negative pressure pump is communicated with one valve port of another two-position three-way valve, and the other two valve ports are respectively communicated with another connector of the vent cover and another connection port at the top of the vacuum barrel by a connecting pipe.

Preferably, the pump valve pipeline mechanism comprises one negative pressure pump and one electromagnetic valve, wherein an air inlet of the negative pressure pump is communicated with the interior of the vacuum barrel by a connecting pipe and a connection port, and an air outlet is communicated with one connector of the vent cover by a connecting pipe; and another connector of the vent cover is communicated with one valve port of the electromagnetic valve by a connecting pipe, and another valve port is communicated with the interior of the vacuum barrel by the connecting pipe and another connection port.

Preferably, the button control assembly includes a button module and a circuit board.

Preferably, the button module is integrated with a Bluetooth module.

The technical effects and advantages of the invention are as follows. According to the water and gas dual-purpose electric erection aid, 1. The device bin is formed by arranging the seal cover to the upper end of the vacuum barrel, and the pump valve pipeline mechanism is arranged in the device bin to communicate the vent cover with the connection port formed in the upper end of the vacuum barrel to form an air suction and discharge loop; a gap between the vent cover and the step groove is sealed by a rubber ring; and meanwhile, the inner wall of the open groove is tightly attached to the outer wall of the button control assembly, so that the sealing inside the seal cover is ensured. Therefore, the whole device can be placed under water for use, capillaries of the penis can be expanded by the temperature of water, the problem of penis swelling caused by the use process is greatly reduced, the comfort level in the use process can be greatly improved, and the use scene can be increased.

2. By arranging a pump valve pipeline with the one negative pressure pump and one electromagnetic valve, a negative pressure pump and two two-position three-way valves, or two negative pressure pumps and one electromagnetic valve, the operation of vacuumizing (exhausting or draining outwards) and recovering the normal vacuum degree in the barrel (namely, filling water or gas into the vacuum barrel) is realized, and it solves the problem of pouring water into the barrel too slowly when the erection aid is positioned under water.

The invention has the core significance that the secret sorrow of men can be solved. Therefore, the life communication between lovers and couples is more harmonious, the derailment probability is reduced, the family harmony and the status equality between the couples are facilitated, the social singleness problem is solved, and the divorce rate is reduced.

In the drawings: 1, a vacuum barrel; 2, a device bin; 21, a seal cover; 22, a pump valve pipeline mechanism; 221, a negative pressure pump; 222, an electromagnetic valve; 223, a two-position three-way valve; 3, an open groove; 4, a button control assembly; 41, a button module; 42 a circuit board; 5, a seal ring; 6, a connection port; 7, a vent cover; 8, a step groove.

DETAILED DESCRIPTION OF THE INVENTION

Hereinafter, technical solutions in the embodiments of the present invention will be described clearly and completely with reference to the accompanying drawings in the embodiments of the present invention. It is obvious that the described embodiments are only a few, but not all, embodiments of the invention. Based on the embodiments of the present invention, all other embodiments obtained by a person of ordinary skill in the art without involving any inventive effort are within the scope of the present invention.

Embodiment 1

Figure 1:
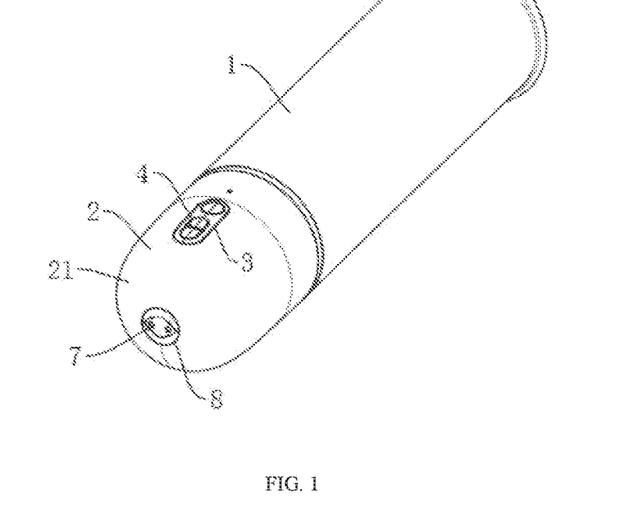
FIG. 1 is a structurally schematic view of the present invention.
Figure 2:
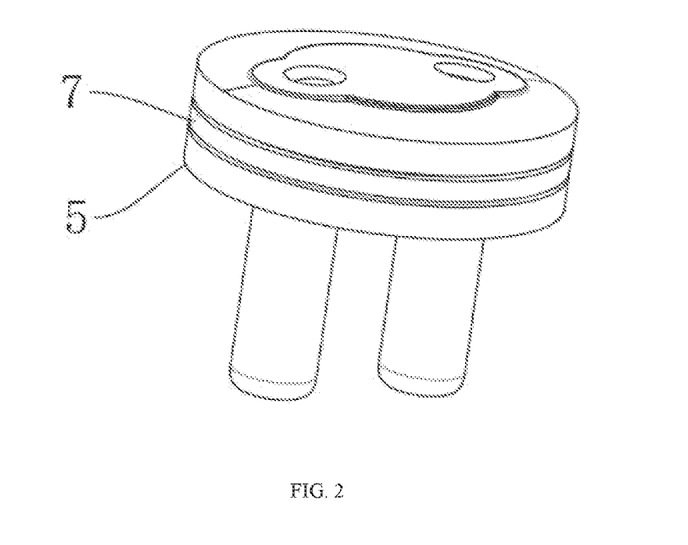
FIG. 2 is a schematic view showing the structure of a vent cover.
Figure 3:
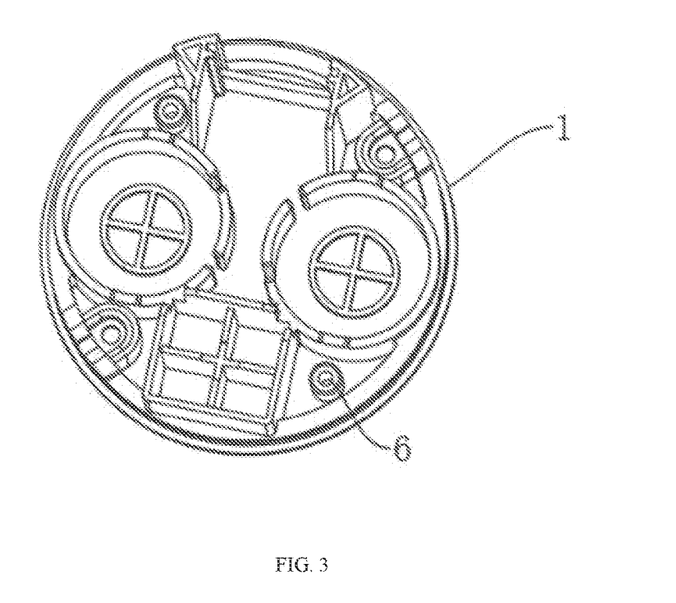
FIG. 3 is a schematic view showing the setting of a connection port at one end of a vacuum barrel.

As shown in FIGS. 1-3, the water and gas dual-purpose electric booster comprises a vacuum barrel 1 and a device bin 2 arranged at the top of the vacuum barrel 1, wherein the device bin 2 comprises a seal cover 21 which covers one end of the vacuum barrel 1 and a pump valve pipeline mechanism 22 arranged in the seal cover 21 and used for vacuumizing or releasing vacuum of the interior of the vacuum barrel 1; and the device bin 2 is fixedly installed with a button control assembly 4 via a support frame, the seal cover 21 is provided with an open groove 3 exposing a button part of the button control assembly 4, and the inner wall of the open groove 3 is tightly attached to the outer wall of the button control assembly 4;

the pump valve pipeline mechanism 22 is communicated with a connection port 6 formed in the top of the vacuum barrel 1 and a vent cover 7 on the seal cover 21 via a connecting pipe, and the vent cover 7 is clamped in a step groove 8 of the seal cover 21 by an outer seal ring 5.

In this embodiment, the connection port 6 is at least provided with two.

The device bin 2 is formed by arranging the seal cover 21 to the upper end of the vacuum barrel 1, and the pump valve pipeline mechanism 22 is arranged in the device bin 2 to communicate the vent cover 7 with the connection port 6 formed in the upper end of the vacuum barrel 1 to form an air suction and air discharge loop; a gap between the vent cover 7 and the step groove 8 is sealed by a rubber ring; and meanwhile, the inner wall of the open groove 3 is tightly attached to the outer wall of the button control assembly 4, so that the sealing inside the seal cover 21 is ensured. Therefore, the whole device can be placed under water for use, capillaries of the penis can be expanded by the temperature of water, the problem of penis swelling caused by the use process is greatly reduced, the comfort level in the use process can be greatly improved, and the use scene can be increased.

Figure 4:
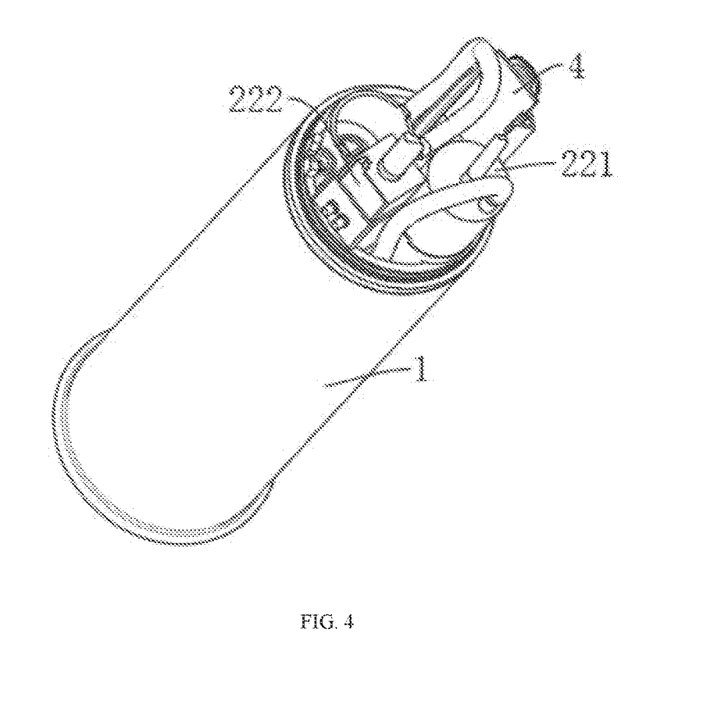
FIG. 4 is a schematic view showing the structure of Embodiment 1.

As shown in FIG. 4, the pump valve pipeline mechanism 22 comprises one negative pressure pump 221 and one electromagnetic valve 222, wherein an air inlet of the negative pressure pump 221 is communicated with the interior of the vacuum barrel 1 by a connecting pipe and a connection port 6, and an air outlet is communicated with one connector of the vent cover 7 by a connecting pipe; and another connector of the vent cover 7 is communicated with one valve port of the electromagnetic valve 222 by a connecting pipe, and another valve port is communicated with the interior of the vacuum barrel 1 by the connecting pipe and another connection port 6.

Figure 5:
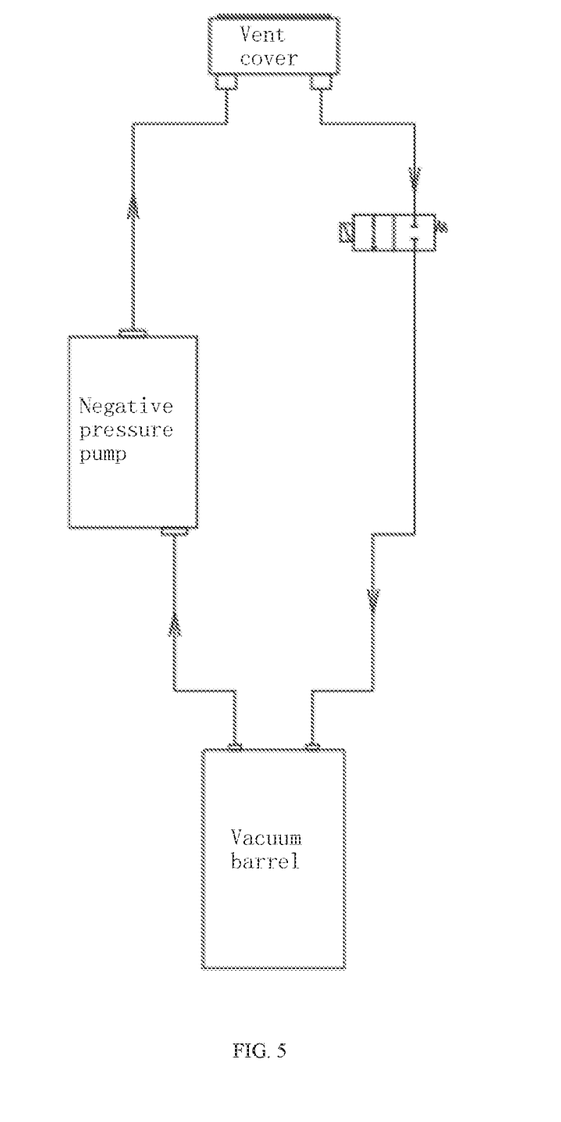
FIG. 5 is a pipeline diagram of Embodiment 1.

According to the pipeline diagram shown in FIG. 5, a pipeline loop for vacuumizing the vacuum barrel 1 is that the electromagnetic valve 222 is closed, the negative pressure pump 221 pumps out air in the vacuum barrel 1 and discharges the air through the vent cover 7, so that vacuum is gradually formed in the vacuum barrel 1, and the effect of helping a user to quickly erect the penis is achieved.

When the vacuum pressure inside the vacuum barrel 1 is released or adjusted, by starting the electromagnetic valve 222, the inside of the vacuum barrel 1 is communicated with the outside atmosphere through the vent cover 7, and a certain amount of air is pressed into the vacuum barrel 1 by the atmospheric pressure so as to achieve the effect of releasing the vacuum inside the vacuum barrel 1 or adjusting the vacuum suction inside the vacuum barrel 1.

The button control assembly 4 includes a button module 41 and a circuit board 42, and the button module 41 is integrated with a Bluetooth module. The device is connected with the mobile device via Bluetooth, so that the function keys can be conveniently and quickly adjusted.

Embodiment 2

Figure 6:
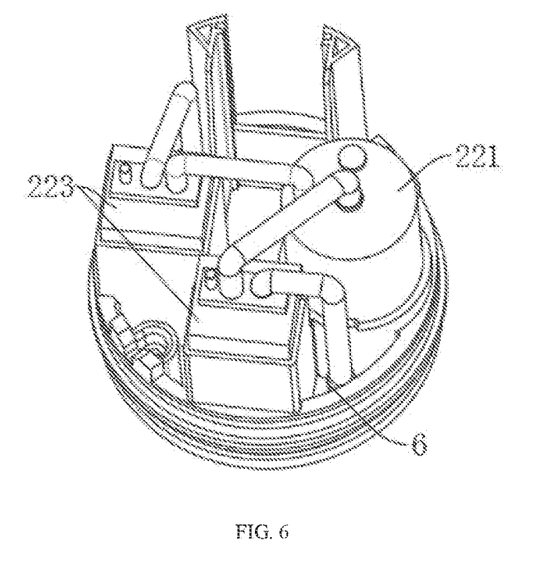
FIG. 6 is a schematic view showing the structure of Embodiment 2.

As shown in FIG. 6, the pump valve pipeline mechanism 22 comprises one negative pressure pump 221 and two two-position three-way valves 223, wherein one connection port 6 is connected with one valve port of one of the two-position three-way valves 223 by a connecting pipe, and the other two valve ports are respectively communicated with the vent cover 7 and the air inlet of the negative pressure pump 221 by the connecting pipe; and the air outlet of the negative pressure pump 221 is communicated with one valve port of another two-position three-way valve 223, and the other two valve ports are respectively communicated with another connector of the vent cover 7 and another connection port 6 at the top of the vacuum barrel 1 by a connecting pipe.

Figure 7:
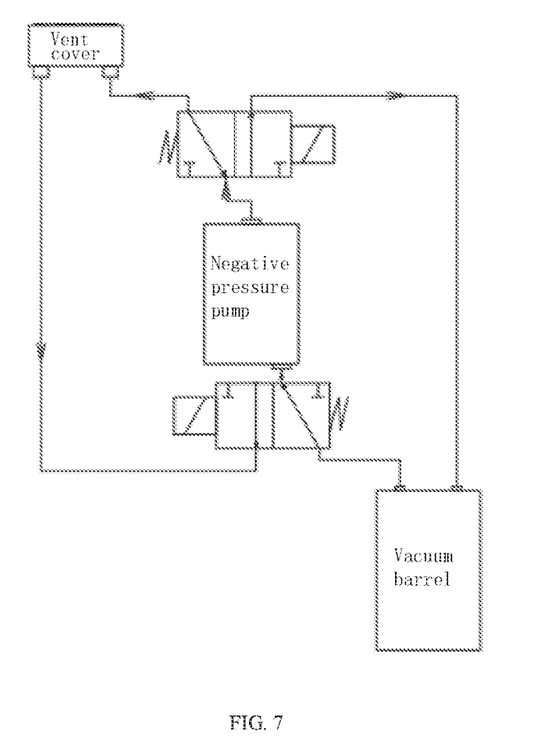
FIG. 7 is a pipeline diagram of Embodiment 2.

According to the pipeline diagram shown in FIG. 7, after the penis is inserted into the vacuum barrel 1, the air is extracted from the vacuum barrel 1, and the vacuum barrel 1 is communicated with the negative pressure pump 221 by a first two-position three-way valve 223. Meanwhile, the negative pressure pump 221 is communicated with the vent cover 7 by a second two-position three-way valve 223, so that the air in the vacuum barrel 1 is sucked outwards, the vacuum barrel 1 tends to be vacuum, and the suction force is generated on the penis to help erection.

When the vacuum pressure inside the vacuum barrel 1 is released or adjusted, one of the two-position three-way valves 223 communicates the vent cover 7 with the air inlet of the negative pressure pump 221, and another two-position three-way valve 223 communicates the air outlet of the negative pressure pump 221 with the vacuum barrel 1, so that external air or water can be conveyed to the inside of the vacuum barrel 1, the pressure inside the vacuum barrel is restored, and the pumping/sucking circuit is adjusted by arranging the two two-position three-way valves. Therefore, the negative pressure pump can pump the air or water in the vacuum barrel and can pump outside air or water into the inside.

When the vacuum barrel 1 is used underwater, the two two-position three-way valves 223 are respectively started for pipeline change, so that the negative pressure pump 221 can suck outside air or water into the vacuum barrel 1, and it solves the problem of pouring water into the barrel too slowly when the erection aid is positioned under water.

Embodiment 3

Figure 8:
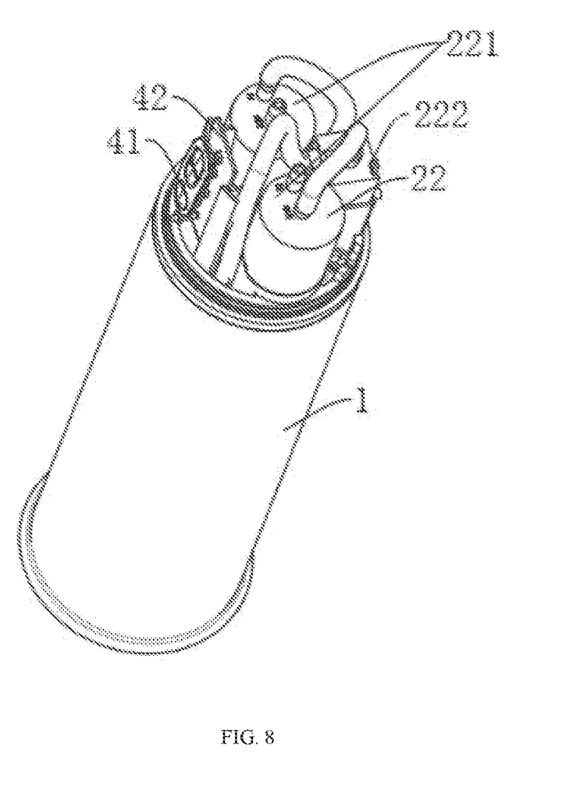
FIG. 8 is a schematic view showing the structure of Embodiment 3.

The difference from the first embodiment is that the pump valve pipeline mechanism 22 shown in FIG. 8 comprises two negative pressure pumps 221 and one electromagnetic valve 222, wherein an air inlet of one negative pressure pump 221 is communicated with one connection port 6 at the top end of the vacuum barrel 1, and an air outlet is communicated with one connector of the vent cover 7 by a connecting pipe; and an air outlet of another negative pressure pump 221 is communicated with another connection port 6 by a connecting pipe, an air inlet is communicated with one valve port of the electromagnetic valve 222 by a connecting pipe, and another valve port is communicated with another connector of the vent cover 7 by a connecting pipe.

Figure 9:
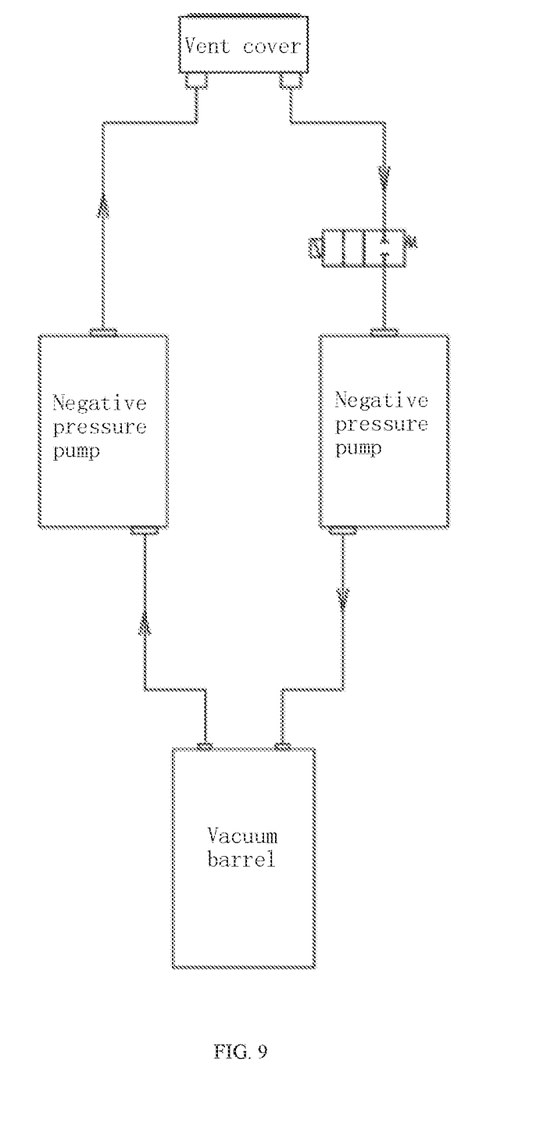
FIG. 9 is a pipeline diagram of Embodiment 3.

According to the pipeline diagram shown in FIG. 9, after the penis is inserted into the vacuum barrel 1, the air is extracted from the vacuum barrel 1, the electromagnetic valve 222 is normally off, and the air in the vacuum barrel 1 is pumped to the outside via the vent cover 7 by one of the negative pressure pumps 221, so that the vacuum barrel 1 tends to be vacuum;

When the vacuum pressure inside the vacuum barrel 1 is released or adjusted, the electromagnetic valve 222 is started to enable another negative pressure pump 221 to convey the air or water from the outside into the vacuum barrel 1 through the vent cover. Therefore, the pressure in the vacuum barrel is quickly recovered.

Compared with Embodiment 1, a single negative pressure pump is additionally arranged. When the device is used underwater, external air or water is pumped into the vacuum barrel by starting the negative pressure pump, and it solves the problem of pouring water into the barrel too slowly when the erection aid is positioned under water.

Finally, it should be noted that the above are only preferred embodiments of the present invention, and are not intended to limit the present invention. Although the present invention has been described in detail with reference to the foregoing embodiments, it is still possible for those skilled in the art to modify the technical solutions described in the foregoing embodiments, or equivalently replace some of the technical features. Any modification, equivalent replacement, improvement, etc. within the spirit and principle of the present invention shall be included within the scope of protection of the present invention.

The invention claimed is:

1. A water and gas dual-purpose electric erection aid, comprising a vacuum barrel (1) and a device bin (2) arranged at a top of the vacuum barrel (1), characterized in that the device bin (2) comprises a seal cover (21) which covers one end of the vacuum barrel (1) and a pump valve pipeline mechanism (22) arranged in the seal cover (21) and used for vacuumizing or releasing vacuum of an interior of the vacuum barrel (1); and the device bin (2) is fixedly installed with a button control assembly (4) via a support frame, the seal cover (21) is provided with an open groove (3) exposing a button part of the button control assembly (4), and an inner wall of the open groove (3) is tightly attached to an outer wall of the button control assembly (4);

the pump valve pipeline mechanism (22) is communicated with two connection ports (6) formed in the top of the vacuum barrel (1) and a vent cover (7) on the seal cover (21) via first to fifth connecting pipes, and the vent cover (7) is clamped in a step groove (8) of the seal cover (21) by an outer seal ring (5); two connection ports are provided in the top of the vacuum barrel (1); the pump valve pipeline mechanism (22) is characterized in one of the following:

a) the pump valve pipeline mechanism (22) comprises two negative pressure pumps (221) and one electromagnetic valve (222), wherein an air inlet of one negative pressure pump (221) is communicated with one of the two connection ports (6) at the top of the vacuum barrel (1), and an air outlet is communicated with a first connector of the vent cover (7) by the first connecting pipe; and an air outlet of another negative pressure pump (221) is communicated with the other of the two connection ports (6) by the second connecting pipe, an air inlet is communicated with one valve port of the electromagnetic valve (222) through the third connecting pipe, and another valve port is communicated with a second connector of the vent cover (7) by the fourth connecting pipe;

b) the pump valve pipeline mechanism (22) comprises one negative pressure pump (221) and two two-position three-way valves (223), wherein the one of the two connection ports (6) is connected with one valve port of one of the two-position three-way valves (223) by the first connecting pipe, and the other two valve ports are respectively communicated with the vent cover (7) and the air inlet of the negative pressure pump (221) by the second connecting pipe and the third connecting pipe; and the air outlet of the negative pressure pump (221) is communicated with one valve port of another two-position three-way valve (223), and the other two valve ports are respectively communicated with the second connector of the vent cover (7) and the other of the two connection ports another connection port (6) on the vacuum barrel (1) by the fourth connecting pipe and the fifth connecting pipe; or c) the pump valve pipeline mechanism (22) comprises one negative pressure pump (221) and an electromagnetic valve (222), wherein an air inlet of the negative pressure pump (221) is communicated with the interior of the vacuum barrel (1) by a connecting pipe and the one of the two connection ports (6), and an air outlet is communicated with the first connector of the vent cover (7) by the second connecting pipe; and the second connector of the vent cover (7) is communicated with one valve port of the electromagnetic valve (222) by the third connecting pipe, and another valve port is communicated with the interior of the vacuum barrel (1) by the fourth connecting pipe and the other of the two connection ports (6).

2. The erection aid as claimed in claim 1, characterized in that the button control assembly (4) comprises a button module (41) and a circuit board (42).

3. The erection aid as claimed in claim 2, characterized in that the button module (41) is integrated with a communication module.

\* \* \* \* \*